US007838694B2

(12) United States Patent
Naidu et al.

(10) Patent No.: US 7,838,694 B2
(45) Date of Patent: Nov. 23, 2010

(54) SEMI-SYNTHESIS AND ISOLATION OF TAXANE INTERMEDIATES FROM A MIXTURE OF TAXANES

(75) Inventors: Ragina Naidu, Burnaby (CA); Samuel Siang Kiang Foo, Vancouver (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 0 days.

(21) Appl. No.: 11/587,407

(22) PCT Filed: Apr. 22, 2005

(86) PCT No.: PCT/US2005/014080

§ 371 (c)(1), (2), (4) Date: Sep. 10, 2007

(87) PCT Pub. No.: WO2005/105767

PCT Pub. Date: Nov. 10, 2005

(65) Prior Publication Data

US 2008/0146824 A1 Jun. 19, 2008

(51) Int. Cl.
C07D 407/00 (2006.01)
(52) U.S. Cl. ...................... 549/510; 549/511
(58) Field of Classification Search ................. 549/510, 549/511
See application file for complete search history.

(56) References Cited

U.S. PATENT DOCUMENTS

| 5,319,112 | A | | 6/1994 | Kingston et al. | |
|---|---|---|---|---|---|
| 5,380,916 | A | * | 1/1995 | Rao | 560/107 |
| 5,530,020 | A | * | 6/1996 | Gunawardana et al. | 514/449 |
| 5,703,247 | A | | 12/1997 | Kingston et al. | |
| 5,808,113 | A | | 9/1998 | Murray et al. | |
| 6,136,989 | A | * | 10/2000 | Foo et al. | 549/510 |
| 6,197,981 | B1 | * | 3/2001 | Liu | 549/510 |
| 6,222,053 | B1 | * | 4/2001 | Zamir et al. | 549/510 |
| 6,576,777 | B2 | * | 6/2003 | Zamir et al. | 549/510 |
| 7,202,370 | B2 | | 4/2007 | Naidu | |
| 2001/0014746 | A1 | | 8/2001 | Holton | |
| 2001/0037020 | A1 | | 11/2001 | Holton | |
| 2001/0041803 | A1 | * | 11/2001 | Kasitu et al. | 549/510 |
| 2008/0033189 | A1 | | 2/2008 | Naidu | |
| 2008/0262250 | A1 | | 10/2008 | Naidu | |

FOREIGN PATENT DOCUMENTS

| EP | 1403261 | | 3/2004 | | |
|---|---|---|---|---|---|
| WO | 98/50378 | | 11/1998 | | |
| WO | 99/54322 | * | 10/1999 | | 549/510 |
| WO | 2004/033442 | | 4/2004 | | |
| WO | 2005/082875 | | 9/2005 | | |
| WO | 2005/118563 | | 12/2005 | | |
| WO | 2006/004708 | | 1/2006 | | |
| WO | 2006/004898 | | 1/2006 | | |

OTHER PUBLICATIONS

Beckvermit et al., "An Improved Method for Separating Paclitaxel and Cephalomannine Using Ozone and Girard Reagents," *J. Org. Chem.*, vol. 61, No. 25, pp. 9038-9040 (1996).
Chen et al., "Synthesis and Biological Evaluation of Novel C-4 Aziridine-Bearing Paclitaxel (Taxol) Analogs," CAPLUS 123:112445, Abstract Only, *Journal of Medicinal Chemistry*, vol. 38, No. 12, pp. 2263-2267 (1995).
Commerçon et al., "Improved Protection and Esterification of a Precursor of the TAXOTERE® and Taxol Side Chains," *Tetrahedron Letters*, vol. 33, No. 36, pp. 5185-5188 (1992).
Final Office action from the U.S. Patent and Trademark Office in U.S. Appl. No. 11/631,466, dated Jul. 20, 2009.
Gennari et al., "Computer-Assisted Design and Synthetic Applications of Chiral Enol Borinates: Novel, Highly Enantioselective Aldol Reagents," *J. Braz. Chem. Soc.*, vol. 9, No. 4, pp. 319-326 (1998).
Gennari et al., "Rationally designed chiral enol borinates: Powerful reagents for the stereoselective synthesis of natural products," *Pure & Appl. Chem.*, vol. 69, No. 3, pp. 507-512 (1997).
International Search Report for PCT/US2005/005953 (mailed Sep. 14, 2005).
International Search Report for PCT/US2005/019697 (mailed Sep. 28, 2005).
International Search Report for PCT/US2005/022844 (mailed Oct. 20, 2005).
International Search Report for PCT/US2005/023224 (mailed Jan. 25, 2006).
Kanazawa et al., "Highly Stereocontrolled and Efficient Preparation of the Protected, Esterification-Ready Docetaxel (Taxotere) Side Chain," *Journal of Organic Chemistry*, vol. 59, pp. 1238-1240 (1994).
Nicolaou et al., "Chemistry and Biology of Taxol," *Angew. Chem. Int. Ed. Engl.*, vol. 33, pp. 15-44 (1994).
Office action from the U.S. Patent and Trademark Office in U.S. Appl. No. 10/590,647, dated Sep. 19, 2008.
Office action from the U.S. Patent and Trademark Office in U.S. Appl. No. 11/631,466, dated Jul. 24, 2008.
Office action from the U.S. Patent and Trademark Office in U.S. Appl. No. 11/631,466, dated Jan. 26, 2009.
Pines et al., "The Stereochemistry of 2,3-Diphenyl-1-methylpropylamine," *Journal of Medical Chemistry*, vol. 10, No. 4, pp. 725-728 (1967).

(Continued)

*Primary Examiner*—Janet L. Andres
*Assistant Examiner*—Raymond Covington
(74) *Attorney, Agent, or Firm*—Klarquist Sparkman, LLP

(57) ABSTRACT

A process is provided for the semi-synthesis and isolation of taxane intermediates useful in the preparation of paclitaxel and docetaxel, in particular, the semi-synthesis and isolation of 10-deacetylbaccatin III, the semi-synthesis of a mixture of 10-deacetylbaccatin III and baccatin III, and protected derivatives thereof, from a mixture of taxanes.

49 Claims, No Drawings

OTHER PUBLICATIONS

Rimoldi et al., "An Improved Method for the Separation of Paclitaxel and Cephalomannine," *Journal of Natural Products*, vol. 59, No. 2, pp. 167-168 (1996).

Office action from the U.S. Patent and Trademark Office in U.S. Appl. No. 11/628,428, dated Sep. 4, 2009.

Office action from the U.S. Patent and Trademark Office in U.S. Appl. No. 11/628,428, dated Feb. 3, 2010.

International Search Report for WO 2005/105767 (mailed Aug. 3, 2005).

* cited by examiner

SEMI-SYNTHESIS AND ISOLATION OF TAXANE INTERMEDIATES FROM A MIXTURE OF TAXANES

PRIORITY CLAIM

This is the §371 U.S. National Stage of International Application No. PCT/US2005/014080, filed Apr. 22, 2005, which was published in English under PCT Article 21(2), which in turn claims the benefit of U.S. patent application Ser. No. 10/831,648, filed Apr. 23, 2004 now abandoned, and U.S. patent application Ser. No. 10/838,653, filed May 4, 2004 now abandoned.

BACKGROUND OF THE INVENTION

1. Field of the Invention

The present invention relates to the semi-synthesis of taxane intermediates useful in the preparation of paclitaxel and docetaxel, in particular, the semi-synthesis and isolation of 10-deacetylbaccatin III, the semi-synthesis of a mixture of 10-deacetylbaccatin III and baccatin III, and derivatives thereof, from a mixture of taxanes.

2. Description of the Related Art

The taxane family of terpenes has received much attention in the scientific and medical community because members of this family have demonstrated broad spectrum anti-leukemic and tumor-inhibitory activity. A well-known member of this family is paclitaxel (1, Taxol).

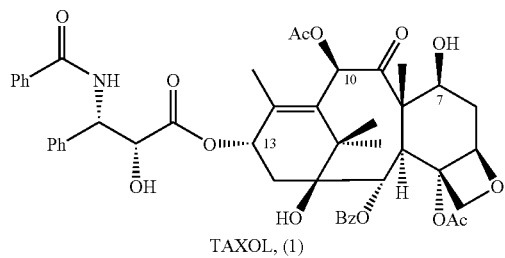

TAXOL, (1)

Paclitaxel was first isolated from the bark of the pacific yew tree (*Taxus brevifolia*) in 1971, and has proved to be a potent natural anticancer agent. For example, paclitaxel has been found to have activity against different forms of leukemia and against solid tumors in the breast, ovary, brain, and lung in humans.

This activity has stimulated an intense research effort over recent years, including the search for other taxanes having similar or improved properties, and the development of synthetic pathways for making taxanes such as paclitaxel. One result from this research effort was the discovery of a synthetic analog of paclitaxel, docetaxel (2, more commonly known as taxotere). As disclosed in U.S. Pat. No. 4,814,470, taxotere has been found to have very good anti-tumor activity and better bio-availability than paclitaxel. Taxotere is similar in structure to paclitaxel, having t-butoxycarbonyl instead of benzoyl on the amino group at the 3' position, and a hydroxyl group instead of the acetoxy group at the C-10 position.

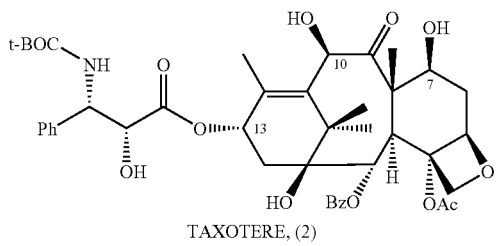

TAXOTERE, (2)

Taxanes are structurally complicated molecules, and the development of commercially viable synthetic methods to make taxanes has been a challenge. A number of semi-synthetic pathways have been developed, which typically begin with the isolation and purification of a naturally occurring material and then its conversion to the taxane of interest. For example, paclitaxel and taxotere may be prepared semi-synthetically from 10-deacetylbaccatin III or baccatin III as set forth in U.S. Pat. No. 4,924,011 to Denis et al. and U.S. Pat. No. 4,924,012 to Colin et al. or by the reaction of a β-lactam and a suitably protected 10-deacetylbaccatin III or baccatin III derivative as set forth in U.S. Pat. No. 5,175,315 to Holton et al. or U.S. patent application Ser. No. 10/683,865, which application is assigned to the assignee of the present invention. 10-deacetylbaccatin III (10-DAB, 3) and baccatin III (BACC III, 4) can be separated from mixtures extracted from natural sources such as the needles, stems, bark or heartwood of numerous *Taxus* species and have the following structures.

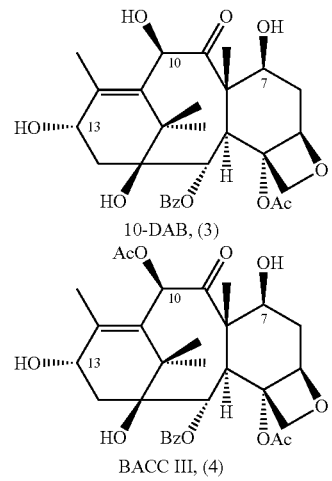

10-DAB, (3)

BACC III, (4)

Although, much of the research towards the semi-synthesis of paclitaxel and taxotere has involved 10-deacetylbaccatin III as the starting material, other taxanes from the *Taxus* species, such as 9-dihydro-13-acetylbaccatin III (9-DHB, 5), present in the Canadian yew (*Taxus Canadensis*), cephalomannine (6), 10-deacetyl taxol (10-DAT, 7), 7-xylosyl taxol (8), 10-deacetyl-7-xylosyl taxol (9), and a number of 7-epi-taxanes have been collected and identified.

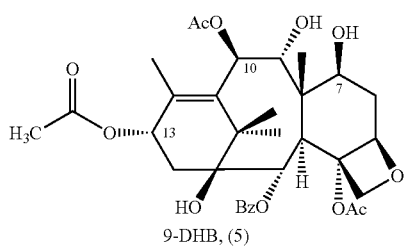

9-DHB, (5)

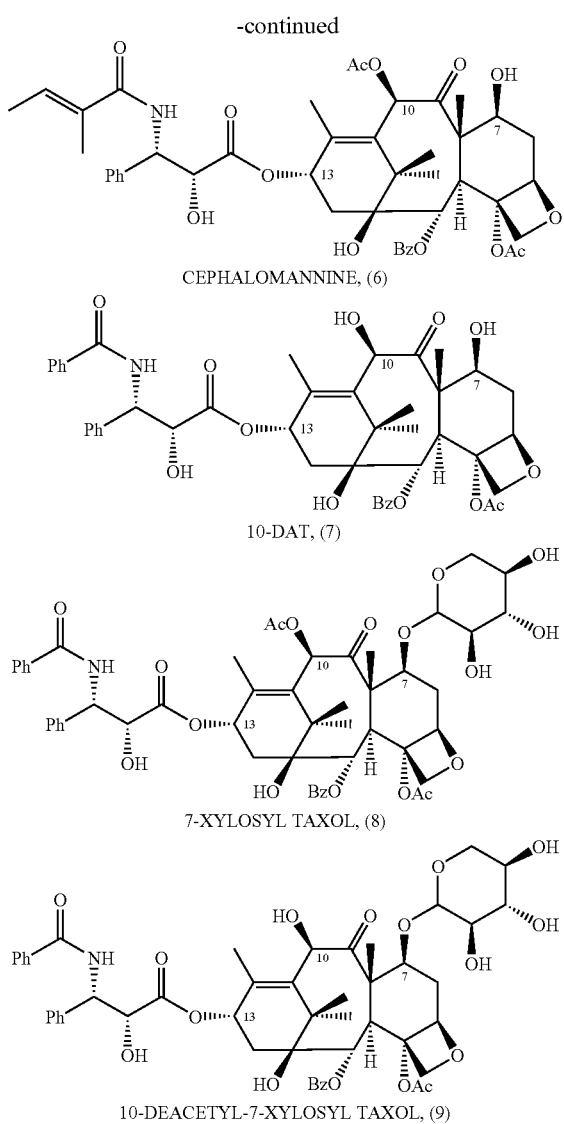

CEPHALOMANNINE, (6)

10-DAT, (7)

7-XYLOSYL TAXOL, (8)

10-DEACETYL-7-XYLOSYL TAXOL, (9)

As disclosed in U.S. patent application Ser. No. 10/695,416, which application is assigned to the assignee of the present invention, U.S. Pat. Nos. 6,576,777 and 6,222,053 to Zamir et al. and U.S. Pat. Nos. 6,175,023 and 6,179,981 to Liu et al., docetaxel and paclitaxel (and suitable starting materials for the synthesis thereof) may also be prepared semi-synthetically from 9-dihydro-13-acetylbaccatin III.

In addition, U.S. Pat. Nos. 5,202,448 and 5,256,801 to Carver et al., U.S. Pat. No. 5,449,790 to Zheng et al. and U.S. Pat. No. 6,281,368 to McChesney et al. disclose processes for converting certain taxanes (namely, paclitaxel, cephalomannine, 10-deacetyl taxol and certain 10-deacetyl taxol derivatives) present in partially purified taxane mixtures into 10-deacetylbaccatin III and baccatin III, which may subsequently be utilized in the foregoing semi-synthetic pathways.

Although there have been many advances in the field, there remains a need for new and improved processes for the preparation of taxane intermediates and their conversion to paclitaxel and docetaxel, in particular, for the preparation of such taxane intermediates from crude and partially purified mixtures comprising a plurality of taxanes. The present invention addresses these needs and provides further related advantages.

BRIEF SUMMARY OF THE INVENTION

According to one aspect of the present invention, the present invention relates to the semi-synthesis and isolation of taxane intermediates useful in the preparation of paclitaxel and docetaxel, in particular, the semi-synthesis and isolation of 10-deacetylbaccatin III, and protected derivatives thereof, from a mixture of taxanes. These processes may thus be utilized to convert a plurality of taxanes present in a crude taxane extract or in a waste taxane solution into taxanes, and taxane derivatives, that can be used to further synthesize paclitaxel and docetaxel. Representative waste taxane solutions may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract.

Generally stated, each processes according to this aspect of the present invention comprise an initial step of cleaving the ester linkages at the C-10 and C-13 positions of each taxane in the initial mixture having an ester linkage at one or both of the C-10 and C-13 positions. Following such initial step, a series of further protection, chromatographic separation, oxidation and deprotection steps are utilized to prepare 10-deacetylbaccatin III, and protected derivatives thereof. 10-deacetylbaccatin III can then be converted to paclitaxel or docetaxel.

More specifically, in a first embodiment, the present invention provides a process for preparing 10-deacetylbaccatin III from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;

(2) separating the taxanes in the first intermediate mixture having a keto substituent at the C-9 position from the taxanes in the first intermediate mixture having a hydroxy group at the C-9 position to yield 10-deacetylbaccatin III and a second intermediate mixture of C-9 hydroxy taxanes;

(3) protecting the hydroxy groups at the C-7 and C-10 positions of each taxane in the second intermediate mixture to yield a third intermediate mixture of C-7 and C-10 protected taxanes;

(4) oxidizing the hydroxy group at the C-9 position of each taxane in the third intermediate mixture to yield a fourth intermediate mixture of C-9 oxidized taxanes; and (5) deprotecting the hydroxy groups at the C-7 and C-10 positions of each taxane in the fourth intermediate mixture to yield 10-deacetylbaccatin III.

In a second embodiment, the order of steps (2) and (3) above are reversed and the present invention provides a process for preparing 10-deacetylbaccatin III from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:
(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;
(2) protecting the hydroxy groups at the C-7 and C-10 positions of each taxane in the first intermediate mixture having a hydroxy group at one or both of the C-7 and C-10 positions to yield a second intermediate mixture of C-7 and C-10 protected taxanes;
(3) separating the taxanes in the second intermediate mixture having a keto substituent at the C-9 position from the taxanes in the second intermediate mixture having a hydroxy group at the C-9 position to yield C-7 and C-10 protected 10-deacetylbaccatin III and a third intermediate mixture of C-9 hydroxy taxanes;
(4) oxidizing the hydroxy group at the C-9 position of each taxane in the third intermediate mixture to yield a fourth intermediate mixture of C-9 oxidized taxanes; and
(5) deprotecting the hydroxy groups at the C-7 and C-10 positions of each taxane in the fourth intermediate mixture to yield 10-deacetylbaccatin III.

In a third embodiment, the present invention provides a process for preparing paclitaxel or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:
(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;
(2) separating the taxanes in the first intermediate mixture having a keto substituent at the C-9 position from the taxanes in the first intermediate mixture having a hydroxy group at the C-9 position to yield 10-deacetylbaccatin III and a second intermediate mixture of C-9 hydroxy taxanes;
(3) protecting the hydroxy groups at the C-7 and C-10 positions of each taxane in the second intermediate mixture to yield a third intermediate mixture of C-7 and C-10 protected taxanes;
(4) oxidizing the hydroxy group at the C-9 position of each taxane in the third intermediate mixture to yield a fourth intermediate mixture of C-9 oxidized taxanes;
(5) deprotecting the hydroxy groups at the C-7 and C-10 positions of each taxane in the fourth intermediate mixture to yield 10-deacetylbaccatin III; and
(6) converting the 10-deacetylbaccatin III obtained from steps (2) and (5) to paclitaxel or docetaxel.

In a fourth embodiment, the present invention provides a process for preparing paclitaxel or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:
(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;
(2) protecting the hydroxy groups at the C-7 and C-10 positions of each taxane in the first intermediate mixture having a hydroxy group at one or both of the C-7 and C-10 positions to yield a second intermediate mixture of C-7 and C-10 protected taxanes;
(3) separating the taxanes in the second intermediate mixture having a keto substituent at the C-9 position from the taxanes in the second intermediate mixture having a hydroxy group at the C-9 position to yield C-7 and C-10 protected 10-deacetylbaccatin III and a third intermediate mixture of C-9 hydroxy taxanes;
(4) oxidizing the hydroxy group at the C-9 position of each taxane in the third intermediate mixture to yield a fourth intermediate mixture of C-9 oxidized taxanes;
(5) deprotecting the hydroxy groups at the C-7 and C-10 positions of each taxane in the fourth intermediate mixture to yield 10-deacetylbaccatin III; and
(6) converting the C-7 and C-10 protected 10-deacetylbaccatin III obtained from step (3) and the 10-deacetylbaccatin III obtained from step (5) to paclitaxel or docetaxel.

According to another aspect of the present invention, the present invention relates to the semi-synthesis of taxane intermediates useful in the preparation of paclitaxel and docetaxel, in particular, the semi-synthesis yields a mixture of 10-deacetylbaccatin III and baccatin III, and derivatives thereof, from a mixture of taxanes. The mixture of 10-deacetylbaccatin III and baccatin III can then be converted to paclitaxel or docetaxel.

According to this aspect of the invention, the processes comprise an initial combined step of protecting the hydroxy group at the C-7 position of each taxane in the initial mixture having a hydroxy group at the C-7 position and cleaving the ester linkage at the C-13 and/or C-10 positions of each taxane in the initial mixture having an ester linkage at the C-13 and/or C-10 positions.

More specifically, in a fifth embodiment, the present invention provides a process for preparing 10-deacetylbaccatin III and baccatin III from an initial mixture of taxanes, wherein the initial mixture comprises 9-dihydro-13-acetylbaccatin III or cephalomannine, and at least one additional taxane selected from paclitaxel, 10-deacetylbaccatin III, baccatin III, 9-dihydro-13-acetylbaccatin III, cephalomannine, 10-deacetyl taxol, 7-xylosyl taxol and 10-deacetyl-7-xylosyl taxol, the process comprising the steps of:
(1) protecting the hydroxy group at the C-7 position of each taxane in the initial mixture having a hydroxy group at the C-7 position and cleaving the ester linkage at the C-13 and C-10 positions of each taxane in the initial mixture having an ester linkage at the C-13 and C-10 positions to yield a first intermediate mixture of C-7 protected taxanes;
(2) oxidizing the hydroxy group at the C-9 position of each taxane in the first intermediate mixture having a hydroxy group at the C-9 position to yield a second intermediate mixture of C-7 protected taxanes; and
(3) deprotecting the hydroxy group at the C-7 position of each taxane in the second intermediate mixture to yield 10-deacetylbaccatin III and baccatin III.

In a six embodiment, the present invention provides a process for preparing paclitaxel or docetaxel from an initial mixture of taxanes, wherein the initial mixture comprises 9-dihydro-13-acetylbaccatin III or cephalomannine, and at least one additional taxane selected from paclitaxel, 10-deacetylbaccatin III, baccatin III, 9-dihydro-13-acetyl-baccatin III, cephalomannine, 10-deacetyl taxol, 7-xylosyl taxol and 10-deacetyl-7-xylosyl taxol, the process comprising the steps of:
(1) protecting the hydroxy group at the C-7 position of each taxane in the initial mixture having a hydroxy group at the C-7 position and cleaving the ester linkage at the C-13 and C-10 positions of each taxane in the initial mixture having an ester linkage at the C-13 and C-10 positions to yield a first intermediate mixture of C-7 protected taxanes;
(2) oxidizing the hydroxy group at the C-9 position of each taxane in the first intermediate mixture having a hydroxy group at the C-9 position to yield a second intermediate mixture of C-7 protected taxanes;
(3) deprotecting the hydroxy group at the C-7 position of each taxane in the second intermediate mixture to yield 10-deacetylbaccatin III and baccatin III; and
(4) converting the 10-deacetylbaccatin III and baccatin III to paclitaxel or docetaxel, wherein the step of converting the 10-deacetylbaccatin III and baccatin III to paclitaxel or docetaxel further comprises protecting the hydroxy group at the C-7 position of each of the 10-deacetylbaccatin III and baccatin III.

In further embodiments of the foregoing processes, the initial mixture comprises: (1) 9-dihydro-13-acetylbaccatin III, and at least two additional taxanes selected from paclitaxel, 10-deacetylbaccatin III, baccatin III, cephalomannine, 10-deacetyl taxol, 7-xylosyl taxol and 10-deacetyl-7-xylosyl taxol; (2) 9-dihydro-13-acetylbaccatin III, and at least three additional taxanes selected from paclitaxel, 10-deacetylbaccatin III, baccatin III, cephalomannine, 10-deacetyl taxol, 7-xylosyl taxol and 10-deacetyl-7-xylosyl taxol; or (3) 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol.

In other further embodiments of the foregoing processes, the initial mixture of taxanes is a waste taxane solution comprising one or more of the following: (1) pooled waste stream fractions collected during a chromatographic separation of a crude or partially purified taxane extract; and (2) pooled waste mother liquors collected during a recrystallization of a crude or partially purified taxane extract. In more specific embodiments: (1) the waste taxane solution comprises pooled waste stream fractions collected during a chromatographic separation of a crude taxane extract; (2) the waste taxane solution comprises pooled waste stream fractions collected during chromatographic separations of both crude and partially purified taxane extracts and pooled waste mother liquors collected during recrystallizations of both crude and partially purified taxane extracts; or (3) the crude and partially purified taxane extracts are obtained from taxane-containing materials from the genus *Taxus*.

These and other aspects of the invention will be apparent upon reference to the following detailed description.

DETAILED DESCRIPTION OF THE INVENTION

I. Definitions

As used herein, the following terms have the following meanings.

"Silica matrix" is a solid media containing a silicate which is used as an adsorbent or column material in chromatographic separations, including (but not limited to) ordinary silica, Florisil, porous silica gels or any physical formulation of a silicate for use in chromatographic procedures.

"Taxane-containing material" refers to selected parts of a plant, plant tissues, cell cultures, microorganisms or extracts with extractable taxanes, including paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol.

"Crude taxane extract" refers to a composition obtained from a taxane-containing material by treating the taxane-containing material with at least one solvent.

"Partially purified taxane extract" refers to a paclitaxel enriched composition obtained from the chromatographic separation and/or recrystallization of a crude or partially purified taxane extract.

"Waste stream fractions" refers to fractions collected following the chromatographic separation and collection of paclitaxel enriched fractions from a crude or partially purified taxane extract by, for example, the process of U.S. Pat. No. 6,136,989.

"Waste mother liquors" refers to mother liquors collected following the recrystallization of a crude or partially purified taxane extract by, for example, the process of U.S. Pat. No. 6,136,989.

"Hydroxy-protecting group" refers to a readily cleavable group bonded to the oxygen of a hydroxy (—OH) group. Examples of hydroxy-protecting groups include, without limitation, formyl, acetyl (Ac), benzyl ($PhCH_2$), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), dichloroacetyl, trichloroacetyl ($OCCCl_3$), 2,2,2-trichloroethoxycarbonyl (Troc), benzyloxymethyl (BOM), tert-butyl (t-Bu), triethylsilyl (TES), trimethylsilyl (TMS), triisopropylsilyl (TIPS), propionyl, isopropionyl, pivalyl, dimethylisopropylsilyl, diethylisopropylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, methoxyethyl, para-methoxyphenyl, tetrahydrofuranyl, alkylsulfonyl and arylsulfonyl. The related term "protected hydroxy group" refers to a hydroxy group that is bonded to a hydroxy-protecting group. General examples of protected hydroxy groups include, without limitation, —O-alkyl, —O-acyl, acetal, and —O-ethoxyethyl, where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloro ethoxycarbonyloxy, benzyloxycarbonyloxy, tert-butoxycarbonyloxy, 1-cyclopropyl ethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, caprylolyoxy, acryloyloxy, methylcarbamoyloxy, phenylcarbamoyloxy, naphthylcarbamoyloxy, and the like. Hydroxy-protecting groups and protected hydroxy groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structure of some hydroxy-protecting groups, as well as nomenclature used to identify those chemical structures.

TABLE 1

| Acetyl (Ac) | 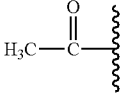 | Acetoxy (—OAc) | 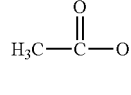 |
|---|---|---|---|
| Dichloroacetyl | 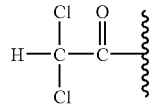 | Dichloroacetoxy | 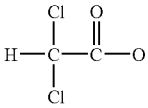 |
| Triethylsilyl (TES) | 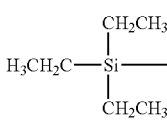 | Triethylsiloxy (—OTES) | 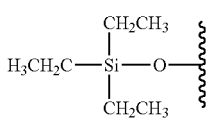 |
| Benzoyl | 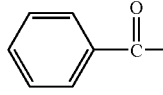 | Benzoyloxy | 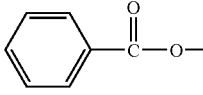 |
| t-Butyloxycarbonyl (tBOC) | 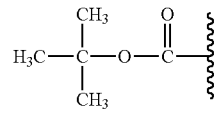 | | |
| t-Butoxycarbonyloxy (—O-tBOC) | 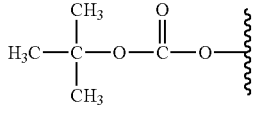 | | |
| para-Methoxyphenyl (PMP) | 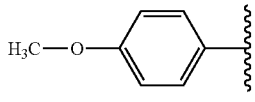 | | |

"Alkyl" refers to a hydrocarbon structure wherein the carbons are arranged in a linear, branched, or cyclic manner, including combinations thereof. Lower alkyl refers to alkyl groups of from 1 to 5 carbon atoms. Examples of lower alkyl groups include methyl, ethyl, propyl, isopropyl, butyl, s- and t-butyl and the like. "Cycloalkyl" is a subset of alkyl and includes cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; propyl includes n-propyl and isopropyl.

"Alkenyl" refers to an alkyl group having at least one site of unsaturation, i.e., at least one double bond.

"Alkynyl" refers to an alkyl group having at least one triple bond between adjacent carbon atoms.

"Alkoxy" and "alkoxyl" both refer to moieties of the formula —O-alkyl. Examples include methoxy, ethoxy, propoxy, isopropoxy, cyclopropyloxy, cyclohexyloxy and the like. Lower-alkoxy refers to groups containing one to four carbons. The analogous term "aryloxy" refers to moieties of the formula —O-aryl.

"Acyl" refers to moieties of the formula —C(=O)-alkyl. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

"Aryl" refers to phenyl or naphthyl. Substituted aryl refers to mono- and poly- substituted phenyl or naphthyl. Exemplary substituents for aryl include one or more of halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

"Heteroaryl" refers to a 5- or 6-membered heteroaromatic ring containing 1-3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0-3 heteroatoms selected from O, N, or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Halogen" refers to fluoro, chloro, bromo or iodo.

"Keto" refers to =O.

II. Process for Preparing and Isolating 10-DAB from a Mixture of Taxanes

As noted above, one aspect of the present invention relates to the semi-synthesis of taxane intermediates useful in the preparation of paclitaxel and docetaxel, in particular, the semi-synthesis of 10-deacetylbaccatin III, and protected derivatives thereof, from an initial mixture of taxanes.

The taxanes present in the initial mixture, namely, 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol, can be represented by the following baccatin molecular framework:

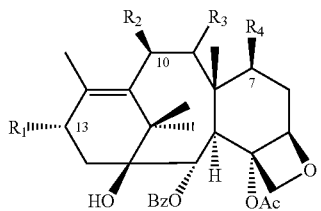

wherein, $R_1$ is —OH, —OAc, N-(2-methyl-2-butenoyl)-(2R, 3S)-3-phenylisoserine or N-benzoyl-(2R, 3S)-3-phenylisoserine, $R_2$ is —OH or —OAc, $R_3$ is —OH or =O, and $R_4$ is —OH or xylosyl. For example, when $R_1$ is —OAc, $R_2$ is —OAc, $R_3$ is —OH and $R_4$ is —OH, the foregoing structure represents 9-dihydro-13-acetylbaccatin III, and when $R_1$ is —OH, $R_2$ is —OAc, $R_3$ is =O and $R_4$ is —OH, the foregoing structure represents baccatin III.

As described in more detail below, 10-deacetylbaccatin III may be prepared from such an initial mixture of taxanes through steps of cleavage, protection, oxidation and deprotection of certain $R_1$, $R_2$, $R_3$ and $R_4$ substituents of the taxanes present in the initial mixture and the chromatographic separation of various taxanes present in the mixture following certain of such steps. For example, in a first embodiment, the present invention provides a process for preparing 10-deacetylbaccatin III from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;

(2) separating the taxanes in the first intermediate mixture having a keto substituent at the C-9 position from the taxanes in the first intermediate mixture having a hydroxy group at the C-9 position to yield 10-deacetylbaccatin III and a second intermediate mixture of C-9 hydroxy taxanes;

(3) protecting the hydroxy groups at the C-7 and C-10 positions of each taxane in the second intermediate mixture to yield a third intermediate mixture of C-7 and C-10 protected taxanes;

(4) oxidizing the hydroxy group at the C-9 position of each taxane in the third intermediate mixture to yield a fourth intermediate mixture of C-9 oxidized taxanes; and (5) deprotecting the hydroxy groups at the C-7 and C-10 positions of each taxane in the fourth intermediate mixture to yield 10-deacetylbaccatin III.

In a second embodiment, the order of steps (2) and (3) are reversed, and the present invention provides a process for preparing 10-deacetylbaccatin III from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;

(2) protecting the hydroxy groups at the C-7 and C-10 positions of each taxane in the first intermediate mixture having a hydroxy group at one or both of the C-7 and C-10 positions to yield a second intermediate mixture of C-7 and C-10 protected taxanes;

(3) separating the taxanes in the second intermediate mixture having a keto substituent at the C-9 position from the taxanes in the second intermediate mixture having a hydroxy group at the C-9 position to yield C-7 and C-10 protected 10-deacetylbaccatin III and a third intermediate mixture of C-9 hydroxy taxanes;

(4) oxidizing the hydroxy group at the C-9 position of each taxane in the third intermediate mixture to yield a fourth intermediate mixture of C-9 oxidized taxanes; and (5) deprotecting the hydroxy groups at the C-7 and C-10 positions of each taxane in the fourth intermediate mixture to yield 10-deacetylbaccatin III.

In general, such cleavage, protection, separation, oxidation and deprotection steps comprise the following methods.

General Method of Cleavage

In one embodiment, the ester linkages at the C-10 and C-13 positions of a taxane in the initial mixture can be cleaved using a base. Suitable bases include, but are not limited to, sodium carbonate, sodium bicarbonate, potassium tert-butoxide, lithium tert-butoxide, LiHMDS, n-butyl lithium, lithium hydroxide, methyl lithium, or a mixture of n-BuLi/K-t-OBu. Typically, K-t-OBu, Li-t-OBu, LiHMDS, n-BuLi, LiOH or $CH_3Li$ can be used. More typically, the step of cleaving the ester linkages at the C-10 and C-13 positions of each taxane in the initial mixture comprises contacting the initial mixture with K-t-OBu.

In another embodiment, the ester linkages at the C-10 and C-13 positions of a taxane in the initial mixture can be cleaved using a reducing salt. The term "reducing salt" refers to a reducing agent in the presence of a Lewis acid. Suitable reducing agents include, but are not limited to, tetrabutylammonium borohydride, lithium borohydride, sodium triacetoxy borohydride, sodium hydride and sodium borohydride. Suitable Lewis acids include, but are not limited to, $SbCl_5$, $ZnCl_2$, $CuCl_2$, $PbCl_2$, $GeCl_2$, $SnBr_2$, $SnI_2$ and $CoBr_2$.

For example, in one embodiment, a mixture of taxanes having ester linkages at one or both of the C-10 and C-13 positions are dissolved in an organic solvent, such as DCM (dichloromethane), THF (tetrahydrofuran), DMF (dimethyl formamide) or DMSO (dimethyl sulfoxide), and cooled to a low temperature under argon atmosphere. To this solution is added a suitable base, and the reaction is stirred until complete consumption of the starting material as evidenced by TLC. The reaction is then worked up as usual and, after purification of the crude mixture by column chromatography using mixtures of DCM/ethyl acetate, the pure C-10 and C-13 deprotected product was obtained.

In another embodiment, the mixture of taxanes having ester linkages at one or both of the C-10 and C-13 positions are dissolved in an organic solvent and a minimum volume of water is added. To this mixture, a suitable reducing agent is added in small portions with vigorous stirring and a catalytic amount of a Lewis acid is added. After completion of the addition, the reaction mixture is stirred for an additional 15 min, then $NH_4Cl$ is added as a concentrated aqueous solution, the layers are then separated and the aqueous phase is extracted with DCM. The combined organic extract is dried and evaporated to give the crude C-10 and C-13 deprotected product. Purification by dry-flash chromatography using DCM/MeOH affords the purified C-10 and C-13 deprotected product.

General Method of Protection

Generally stated, the hydroxy groups at the C-7 and C-10 positions of a taxane can be selectively protected by contacting the intermediate mixture with a base and a hydroxy-protecting group in an organic solvent. The intermediate mixture can be the immediate reaction mixture resulted from an initial cleavage of the ester groups at the C-10 and C-13 position and comprises taxanes having C-9 keto and C-9 hydroxy groups. Alternatively, the intermediate mixture comprises only those taxanes having C-9 hydroxy groups after a separation step.

The hydroxy groups at the C-7 and C-10 positions of a taxane can be selectively protected using any of a variety of hydroxy protecting groups, such as alkylating agents, acylating agents and silylating agent. For example, the C-7 and C-10 hydroxy groups may be silylated using any of a variety of common silylating agents including, but not limited to, tri(hydrocarbonyl)silyl halides and tri(hydrocarbonyl)silyl triflates. The hydrocarbonyl moieties of these compounds may be substituted or unsubstituted and preferably are substituted or unsubstituted alkyl or acyl. More specifically, the C-7 and C-10 hydroxy groups can be selectively silylated, for example, using silylating agents such as tribenzylsilyl chloride, trimethylsilyl chloride, triethylsilyl chloride, dimethylisopropylsilyl chloride, dimethylphenylsilyl chloride and the like. Alternatively, selective acylation of the C-7 and C-10 hydroxy groups can be achieved using any of a variety of common acylating agents, including, but not limited to substituted and unsubstituted carboxylic acid derivatives, e.g., carboxylic acid halides, anhydrides, dicarbonates, isocyanates and haloformates. Typically, the C-7 and C-10 hydroxy groups can be selectively acylated, for example, with di-tert-butyl dicarbonate, dibenzyl dicarbonate, diallyl dicarbonate, 2,2,2-trichloroethyl chloroformate, benzyl chloroformate or dichloroacetyl chloride or another common acylating agent. More typically, tert-butoxycarbonyl, benzyloxycarbonyl, 2,2,2-trichloroethoxycarbonyl, dichloroacetyl and acetyl are used.

In the present invention, these protecting reactions are carried out in the presence of a base, such as, for example, Li-t-OBu, K-t-OBu, n-BuLi, a mixture of n-BuLi/K-t-OBu, LiOH, pyridine, DMAP or TEA. In a specific embodiment, the base is DMAP and the hydroxy-protecting group is tert-butoxycarbonyl.

Exemplary reaction conditions are as follows: a mixture of taxanes is dissolved in an organic solvent, such as anhydrous DCM (dichloromethane) or THF (tetrahydrofuran) or DMF (dimethyl formamide) or DMSO (dimethyl sulfoxide) under an argon atmosphere at low temperature. To this solution is added DMAP (dimethylaminopyridine) or any other base, such as Li-t-OBu or K-t-OBu, followed by an acylating agent, such as di-tert-butyl dicarbonate, or an alkylating agent, such as triethyl silyl chloride or any other chloride containing a hydroxy-protecting group. The mixture is left at low to room temperature until complete consumption of the starting material, as visualized by TLC. The mixture is then quenched with cold water and extracted thrice with DCM. The organic layer is washed with water and then with brine to remove unwanted salts. The organic layer may then be dried and evaporated under vacuum, and the residue recrystallized or column chromatographed with DCM/EtOAc mixtures to afford C-7 and C-10 protected taxanes.

General Method of Separation

Normal phase silica chromatography may be utilized to separate a mixture of taxanes into the following two groups: taxanes having a keto substituent at the C-9 position (i.e., protected 10-DAB derivatives) and taxanes having a hydroxy group at the C-9 position. As used herein, silica chromatography generally refers to the process of contacting a sample dissolved in a feed solvent with a silica matrix then eluting the silica matrix with an eluting solvent to obtain a fraction enriched with a desired component.

The dimensions of the silica column are selected according to the quantity and purity of the solids to be separated. In one embodiment of a pilot scale process, about 250 grams of solids are dissolved in about 0.75 liters of feed solvent which is then chromatographed over a Silica column of about 1.5-inches×10-feet. In another embodiment, about 40-50 kg of solids are dissolved in about 100-200 liters of feed solvent, and chromatographed over a Silica column of about 18-inches×10-feet.

It has also been shown that a layer of about 1-15 cm of Celite, preferably about 2-8 cm, on top of the silica column is recommended as a column prefilter which substantially decreases the loading time of the sample. It has further been shown that the optimal eluting solvent for the Silica column can be a hexane/acetone or DCM/ethyl acetate or DCM/methanol mixtures.

General Method of Oxidation

Generally stated, the hydroxy group at the C-9 position of each taxane in an intermediate mixture can be selectively oxidized by contacting the intermediate mixture with an oxidizing agent selected from the group consisting of 4-(dimethylamino)pyridinium chlorochromate, pyridinium chlorochromate, chromium (IV) oxide-silica gel, chromium (IV) oxide-acetic acid, bromine, dimethyl sulfoxide-dicyclohexylcarbodiimide, and manganese dioxide with dichloro(p-cymene)-ruthenium (II). In specific embodiments, the oxidizing agent is chromium (IV) oxide-silica gel.

For example, C-7 protected taxanes are dissolved in an organic solvent and treated with an oxidant at low to room temperature conditions. The reaction is stirred until all the starting material is consumed, as evidenced by TLC. The reaction is then worked up as usual to yield a mixture of C-9 oxidized taxanes. Such mixture can be further purified by column chromatography or crystallized from a suitable solvent.

General Method of Deprotection

Generally stated, the hydroxy groups at the C-7 and C-10 positions of each taxane in an intermediate mixture are separately deprotected.

C-10 protected taxanes may be deprotected using a base. Suitable bases include sodium carbonate, sodium bicarbonate, potassium tert-butoxide, lithium tert-butoxide, LiHMDS, n-butyl lithium, lithium hydroxide, methyl lithium or a mixture of n-BuLi/K-t-OBu. For example, C-10 protected taxanes are dissolved in an organic solvent and cooled to a low temperature under argon atmosphere. To this solution is added a suitable base, and the reaction is stirred until complete consumption of the starting material as evidenced by TLC. The reaction is then worked up as usual and, after purification of the crude mixture by column chromatography using mixtures of DCM/ethyl acetate, the pure C-10 deprotected product was obtained.

C-7 protected taxanes may be deprotected using an acid. Suitable acids include HF, HCl, TFA and acetic acid. For example, C-7 protected taxanes are dissolved in pyridine or an organic solvent at room temperature and treated with an acid, such as HF, HCl, TFA or acetic acid. The reaction is stirred at this temperature until complete consumption of the starting materials, as evidenced by TLC. The reaction is worked up as usual to give the C-7 deprotected product, which could be further purified by column chromatography or crystallized from a suitable solvent.

In a specific embodiment, the step of deprotecting the hydroxy groups at the C-7 and C-10 positions of each taxane in an intermediate mixture comprises: (1) deprotecting the hydroxy groups at the C-10 positions of each taxane in an intermediate mixture comprises contacting the intermediate mixture with a base selected from the group consisting of LiOH, n-BuLi, Li-t-OBu, $CH_3Li$, K-t-OBu and LiHMDS, and (2) deprotecting the hydroxy groups at the C-7 position of each taxane in the fourth intermediate mixture comprises contacting the fourth intermediate mixture with an acid selected from the group consisting of HF, TFA, HCl and acetic acid.

III. Process for Preparing 10-DAB and BACC III from a Mixture of Taxanes

As noted above, another aspect of the present invention relates to the semi-synthesis of taxane intermediates useful in the preparation of paclitaxel and docetaxel, in particular, the semi-synthesis of 10-deacetylbaccatin III and baccatin III, and derivatives thereof, from an initial mixture of taxanes.

The taxanes present in the initial mixture, namely, 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol, contain the following baccatin molecular framework:

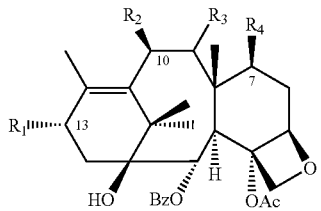

wherein $R_1$ is —OH, —OAc, N-(2-methyl-2-butenoyl)-(2R, 3S)-3-phenylisoserine or N-benzoyl-(2R, 3S)-3-phenylisoserine, $R_2$ is —OH or —OAc, $R_3$ is —OH or =O, and $R_4$ is —OH or xylosyl. For example, when $R_1$ is —OAc, $R_2$ is —OAc, $R_3$ is —OH and $R_4$ is —OH, the foregoing structure represents 9-dihydro-13-acetylbaccatin III, and when $R_1$ is —OH, $R_2$ is —OAc, $R_3$ is =O and $R_4$ is —OH, the foregoing structure represents baccatin III.

As described in more detail below, 10-deacetylbaccatin III and baccatin III may be prepared from such an initial mixture of taxanes through the protection, cleavage, oxidation and deprotection of certain $R_1$, $R_2$, $R_3$ and $R_4$ substituents of the taxanes present in the initial mixture. For example, the present invention provides a process for preparing 10-deacetylbaccatin III and baccatin III from an initial mixture of taxanes, wherein the initial mixture comprises 9-dihydro-13-acetylbaccatin III or cephalomannine, and at least one additional taxane selected from paclitaxel, 10-deacetylbaccatin III, baccatin III, 9-dihydro-13-acetylbaccatin III, cephalomannine, 10-deacetyl taxol, 7-xylosyl taxol and 10-deacetyl-7-xylosyl taxol, the process comprising the steps of:

(1) protecting the hydroxy group at the C-7 position of each taxane in the initial mixture having a hydroxy group at the C-7 position and cleaving the ester linkage at the C-13 position of each taxane in the initial mixture having an ester linkage at the C-13 position to yield a first intermediate mixture of C-7 protected taxanes;

(2) oxidizing the hydroxy group at the C-9 position of each taxane in the first intermediate mixture having a hydroxy group at the C-9 position to yield a second intermediate mixture of C-7 protected taxanes; and (3) deprotecting the hydroxy group at the C-7 position of each taxane in the second intermediate mixture to yield 10-deacetylbaccatin III and baccatin The combined step of protection and cleavage can be carried out according to the following method:

Combined Step of Protection and Cleavage

The hydroxy group at the C-7 position of a taxane can be selectively protected using any of a variety of hydroxy protecting groups, such as acetal, ketal, silyl, and removable acyl protecting groups. For example, the C-7 hydroxy group may be silylated using any of a variety of common silylating agents including, but not limited to, tri(hydrocarbonyl)silyl halides and tri(hydrocarbonyl)silyl triflates. The hydrocarbonyl moieties of these compounds may be substituted or unsubstituted and preferably are substituted or unsubstituted alkyl or acyl. More specifically, the C-7 hydroxy group can be selectively silylated, for example, using silylating agents such as tribenzylsilyl chloride, trimethylsilyl chloride, triethylsilyl chloride, dimethylisopropylsilyl chloride, dimethylphenylsilyl chloride and the like. Alternatively, selective acylation of the C-7 hydroxy group can be achieved using any of a variety of common acylating agents, but not limited to substituted and unsubstituted carboxylic acid derivatives, e.g., carboxylic acid halides, anhydrides, dicarbonates, isocyanates and haloformates. More specifically, the C-7 hydroxy group can be selectively acylated, for example, with di-tert-butyl dicarbonate, dibenzyl dicarbonate, diallyl dicarbonate, 2,2,2-trichloroethyl chloroformate, benzyl chloroformate or dichloroacetyl chloride or another common acylating agent.

In the present invention, these protecting reactions are carried out in the presence of a base, such as, for example, Li-t-OBu, K-t-OBu, n-BuLi, a mixture of n-BuLi/K-t-OBu, LiOH, pyridine, DMAP or TEA. In addition to aiding in the protection of the C-7 hydroxy group, depending upon the amount of base utilized, the base also cleaves any ester linkage at the C-13 position and, may also cleave any ester linkage at the C-10 position.

Exemplary reaction conditions are as follows: a mixture of taxanes is dissolved in anhydrous DCM (dichloromethane) or THF (tetrahydrofuran) or DMF (dimethyl formamide) or DMSO (dimethyl sulfoxide) under an argon atmosphere at low temperature. To this solution is added DMAP (dimethylaminopyridine) or any other lithium or potassium base, such as Li-t-OBu, K-t-OBu, n-BuLi, a mixture of n-BuLi/K-t-OBu, or LiOH, followed by an acylating agent, such as di-tert-butyl dicarbonate, or an alkylating agent, such as triethyl silyl chloride or any other chloride containing a hydroxy-protecting group. The mixture is left at low to room temperature until complete consumption of the starting material, as visualized by TLC. In addition, excess amounts of the base may be added to this mixture, in the same pot, to ensure cleavage of any ester linkages at the C-13 and/or C-10 positions. The mixture is then quenched with cold water and extracted thrice with DCM. The organic layer is washed with water and then with brine to remove unwanted salts. The organic layer may then be dried and evaporated under vacuum, and the residue recrystallized or column chromatographed with DCM/EtOAc mixtures to afford a mixture of C-7 protected taxanes.

The step of oxidation can be carried out in a similar manner as described above.

The step of deprotection can be carried out in the following method:

General Method of Deprotection

C-7 protected taxanes may be deprotected using an acid. Suitable acids include HF, HCl, TFA and acetic acid.

For example, C-7 protected taxanes are dissolved in pyridine or an organic solvent at room temperature and treated with an acid, such as HF, HCl, TFA or acetic acid. The reaction is stirred at this temperature until complete consumption of the starting materials, as evidenced by TLC. The reaction is worked up as usual to give the deprotected product, which could be further purified by column chromatography or crystallized from a suitable solvent.

IV. Initial Mixture of Taxanes

As noted above, the processes of the present invention may be utilized for high yield and large scale conversion of taxanes present in a waste taxane solution into taxanes intermediates, namely, 10-deacetylbaccatin III and baccatin III protected derivatives thereof, that can be used to further synthesize paclitaxel and docetaxel. Such a waste taxane solution may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract.

Such waste taxane solutions may be obtained by a number of different methods, such as, for example, the methods disclosed in U.S. Pat. No. 6,136,989 to Foo et al., and other references cited therein, which patent is incorporated herein by reference in its entirety. A representative method of obtaining a waste taxane solution, which comprises pooled waste stream fractions, comprises the following extraction and column chromatography steps.

Starting Taxane-Containing Material

A suitable taxane-containing material is any tissue that contains a high taxane content. Examples of suitable taxane-containing material include tissues from various species of Yew plants comprising the genus *Taxus*, most preferably the roots and needles of ornamental Yew plants such as *T. canadensis*, *T. x media* spp *Hicksii*, *T. x* dark green spreader and Hill., *T. chinensis*, *T. wallichiana*, *T. cuspidata*, *T. globosa*, *T. sumatrana*, *T. marei* and *T. floridana*, and the bark of *T. brevifolia* or *T. yunnanensis*. Other suitable material include cultures of plant tissues obtained from a *Taxus* species.

In a typical practice, such as set forth in U.S. Pat. No. 6,139,989, the taxane-containing material is either pulverized, chipped or otherwise ground into small pieces so as to increase efficiency of a solvent extraction. The taxane-containing material may also optionally be dried. Taxane-containing cell culture, cells, microorganisms and fermentation broths will typically be concentrated prior to solvent extraction. Cells and microorganisms can be processed as whole cells or cell paste or pulver.

Extraction

The taxane-containing material may be initially extracted by contacting the material with an organic solvent, usually for a prolonged period of at least 8 hours and typically for about 3 days with or without physical agitation to promote formation of a crude organic extract containing a plurality of taxanes. The extraction may employ any of the solvent systems that are known to be used for the extraction of paclitaxel, including but not limited to, acetone, methanol, ethanol, ethyl acetate, methylene chloride, chloroform, mixtures thereof, and mixtures containing an aqueous component of up to 60%. These solvents are typically added in an amount of about 4-20 liter per kg of the taxane-containing material to prepare the crude organic extract. Reference is made for example, to U.S. Pat. No. 6,136,989 and the publications cited therein which provide a non-exclusive description of several solvent systems that may be used to prepare an organic extract containing a plurality of taxanes.

In one embodiment, the organic solvent is a polar organic solvent, typically an alcohol. For some embodiments, methanol is preferred because of its low cost, ease of removal and efficiency of taxane extraction. In one embodiment, about 6-15 liters of methanol is added for every kg of taxane-containing material to be extracted. The extraction is accelerated by agitating the taxane-containing material, for example, by stirring or percolating the methanol with the taxane-containing material for about 1-5 days at a temperature between room temperature and about 60° C., most typically at about 40° C. When the taxane-containing material contains a paclitaxel content of at least 0.005%, methanol extraction for three days as described above recovers at least 90% of the available paclitaxel from the taxane-containing material, in addition to a plurality of other taxanes, to form a crude methanol extract containing about 0.1-0.5% paclitaxel and having an overall solid content of about 0.5-5% (w/v).

The large volume of methanol extract thus obtained is optionally concentrated, typically about 10-30 fold by evaporation to obtain a methanol extract concentrate having a solid content of about 100-400 g/L.

Liquid-Liquid Extraction

The crude organic extract may be subsequently enriched for taxanes by performing 1-3 liquid-liquid extractions by mixing the organic extract with a non-miscible, organic solvent to form a two phase system wherein one phase contains the plurality of taxanes. Generally, the two phase system includes a polar phase. Optionally, the taxane-containing phase is selected and concentrated by evaporation to form a concentrated extract having a solid content of about 100-400 g/L and a paclitaxel purity of about 1-4%. In some embodiments, water is included to help remove preferentially water soluble materials and the less polar solvent is selected to remove undesirable compounds such as waxes, lipids, pigments, and sterols that are found in different amounts depending on the taxane-containing material used. Typical solvents for liquid-liquid partitioning include hexane, hexanes, and methylene chloride. Methylene chloride has generally been found to be suitable for liquid-liquid extraction of taxane-containing material especially when the solvent used for the crude organic extract is an alcohol.

The concentrated extract obtained is optionally evaporated and the residue is re-dissolved in a solvent for loading onto a silica chromatography matrix.

Other example methods of performing a liquid-liquid extraction are illustrated in U.S. Pat. Nos. 5,475,120, 5,380,916, and 5,670,673 to Rao and references cited therein, and also in U.S. Pat. Nos. 5,618,538 and 5,480,639 to ElSohly et al. and references cited therein. These methods or variants thereof may alternatively be used in lieu of the embodiments described. Furthermore, liquid-liquid extraction may be omitted altogether when a plant extract containing high taxane levels is obtained by other methods such as for example, by intervening precipitation, crystallization or chromatography steps. One example of such a method is found in PCT Publication Nos. WO 98/07712 by Zamir et al, which uses a precipitation step immediately after obtaining an initial organic extract to obtain a paclitaxel fraction that may be about 1% or higher.

Silica Gel Column Chromatography

As further set forth in U.S. Pat. No. 6,136,989, the concentrated extract may be further purified by normal phase silica chromatography. As used herein, silica chromatography generally refers to the process of contacting a sample dissolved in a feed solvent with a silica matrix then eluting the silica matrix with an eluting solvent to obtain a fraction enriched with a desired component.

The dimensions of the first silica column are selected according to the quantity and purity of the solids to be separated. In one embodiment of a pilot scale process, about 250 grams of solids are dissolved in about 0.75 liters of feed solvent which is then chromatographed over a Silica column of about 1.5-inches×10-feet. In another embodiment, about 40-50 kg of solids are dissolved in about 100-200 liters of feed solvent, and chromatographed over a Silica column of about 18-inches×10-feet.

It has also been shown that a layer of about 1-15 cm of Celite, preferably about 2-8 cm, on top of the silica column is recommended as a column prefilter which substantially decreases the loading time of the sample. It has further been shown that the optimal eluting solvent for the Silica column should be a hexane/acetone mixture at a ratio of about 3:1 or a DCM/ethyl acetate mixture at a ratio of about 7:3. The "heart cut" fractions containing at least 2% paclitaxel are pooled and further purified, for example, according to the process set forth in U.S. Pat. No. 6,136,989. The remaining waste stream fractions, which contain a plurality of taxanes, including, paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol are pooled into a waste taxane solution for further processing according to the present invention.

Further Purification Steps

As set forth in more detail in U.S. Pat. No. 6,139,989, the paclitaxel enriched "heart cut" fractions obtained from the foregoing chromatography step may be further purified through one or more additional chromatographic or recrystallization steps. Any waste stream fractions or waste mother liquors collected during such additional purification steps may also be pooled and added to the waste taxane solution for further processing according to the present invention.

V. Process for Preparing Paclitaxel or Docetaxel

As noted above, the 10-deacetylbaccatin III, and protected derivatives thereof, prepared from an initial mixture of taxanes according to the foregoing processes may be utilized to further synthesize paclitaxel and docetaxel. In this way, in a third embodiment, the present invention provides an overall process for preparing paclitaxel or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;

(2) separating the taxanes in the first intermediate mixture having a keto substituent at the C-9 position from the taxanes in the first intermediate mixture having a hydroxy group at the C-9 position to yield 10-deacetylbaccatin III and a second intermediate mixture of C-9 hydroxy taxanes;

(3) protecting the hydroxy groups at the C-7 and C-10 positions of each taxane in the second intermediate mixture to yield a third intermediate mixture of C-7 and C-10 protected taxanes;

(4) oxidizing the hydroxy group at the C-9 position of each taxane in the third intermediate mixture to yield a fourth intermediate mixture of C-9 oxidized taxanes;

(5) deprotecting the hydroxy groups at the C-7 and C-10 positions of each taxane in the fourth intermediate mixture to yield 10-deacetylbaccatin III; and (6) converting the 10-deacetylbaccatin III obtained from steps (2) and (5) to paclitaxel or docetaxel.

In addition, in a fourth embodiment, the present invention provides a process for preparing paclitaxel or docetaxel from an initial mixture of taxanes, wherein the initial mixture comprises 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process comprising the steps of:

(1) cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;

(2) protecting the hydroxy groups at the C-7 and C-10 positions of each taxane in the first intermediate mixture having a hydroxy group at one or both of the C-7 and C-10 positions to yield a second intermediate mixture of C-7 and C-10 protected taxanes;

(3) separating the taxanes in the second intermediate mixture having a keto substituent at the C-9 position from the taxanes in the second intermediate mixture having a hydroxy group at the C-9 position to yield C-7 and C-10 protected 10-deacetylbaccatin III and a third intermediate mixture of C-9 hydroxy taxanes;

(4) oxidizing the hydroxy group at the C-9 position of each taxane in the third intermediate mixture to yield a fourth intermediate mixture of C-9 oxidized taxanes;

(5) deprotecting the hydroxy groups at the C-7 and C-10 positions of each taxane in the fourth intermediate mixture to yield 10-deacetylbaccatin III; and (6) converting the C-7 and C-10 protected 10-deacetylbaccatin III obtained from step (3) and the 10-deacetylbaccatin III obtained from step (5) to paclitaxel or docetaxel.

10-deacetylbaccatin III, and protected 10-deacetylbaccatin III, may be converted to paclitaxel and docetaxel by a number of different methods, such as, for example, the methods disclosed in U.S. Pat. Nos. 4,924,011, 4,924,012, 5,175,315 and 5,466,834, which patents are incorporated herein by reference in their entirety, and U.S. patent application Ser. No. 10/683,865, which application is assigned to the assignee of the present invention and is incorporated herein by reference in its entirety.

In a further embodiment, a mixture of 10-deacetylbaccatin III and baccatin III prepared from an initial mixture of taxanes according to the foregoing process can be converted to paclitaxel and docetaxel. To that end, the present invention provides an overall process for preparing paclitaxel or docetaxel from an initial mixture of taxanes, wherein the initial mixture comprises 9-dihydro-13-acetylbaccatin III or cephalomannine, and at least one additional taxane selected from paclitaxel, 10-deacetylbaccatin III, baccatin III, 9-dihydro-13-acetylbaccatin III, cephalomannine, 10-deacetyl taxol, 7-xylosyl taxol and 10-deacetyl-7-xylosyl taxol, the process comprising the steps of:

(1) protecting the hydroxy group at the C-7 position of each taxane in the initial mixture having a hydroxy group at the C-7 position and cleaving the ester linkage at the C-13 position of each taxane in the initial mixture having an ester linkage at the C-13 position to yield a first intermediate mixture of C-7 protected taxanes;

(2) oxidizing the hydroxy group at the C-9 position of each taxane in the first intermediate mixture having a hydroxy group at the C-9 position to yield a second intermediate mixture of C-7 protected taxanes;

(3) deprotecting the hydroxy group at the C-7 position of each taxane in the second intermediate mixture to yield 10-deacetylbaccatin III and baccatin III; and (4) converting the 10-deacetylbaccatin III and baccatin III to paclitaxel or docetaxel, wherein the step of converting the 10-deacetylbaccatin III and baccatin III to paclitaxel or docetaxel further comprises protecting the hydroxy group at the C-7 position of each of the 10-deacetylbaccatin III and baccatin III.

10-deacetylbaccatin III and baccatin III may be converted to paclitaxel and docetaxel by a number of different methods, such as, for example, the methods disclosed in U.S. Pat. Nos. 4,924,011, 4,924,012, 5,175,315 and 5,466,834, which patents are incorporated herein by reference in their entirety, and U.S. patent application Ser. No. 10/683,865, which application is assigned to the assignee of the present invention and is incorporated herein by reference in its entirety.

EXAMPLES

The following Examples disclose specific processes for synthesizing and isolating 10-deacetylbaccatin III, or a mixture of 10-deacetylbaccatin III and baccatin III, and protected derivatives thereof, from a solution containing a plurality of taxanes, and their subsequent conversion to paclitaxel and docetaxel. Unless otherwise noted, all scientific and technical terms have the meanings as understood by one of ordinary skill in the art.

Example 1

Extraction of Taxanes from *Taxus Canadensis*

Needles from the Canadian yew (*Taxus Canadensis*) were collected in Quebec. The dried needles (3 kg) were extracted by percolation with methanol at room temperature three times using 10L, 6L and 6L volumes of methanol in a glass container equipped with a filter at the bottom with a tap. The extraction with each subsequent volume of methanol was left for 24 hours and the mixture was filtered into an erlenmeyer flask by opening the tap at the bottom to give a crude extract. The crude methanolic extracts were combined and concentrated to give about 1.1L of a crude methanol extract concentrate.

Example 2A

Filtration of the Crude Extract

A silica/charcoal filter was prepared as follows. Norit SA3 charcoal (0.5 kg: 100 mesh—Aldrich) was mixed with celite (0.5 kg: AC 2098T—Anachemia) and placed into a coarse scintered glass funnel. The charcoal-celite mixture was soaked with dichloromethane:methanol (9:1) and washed with an additional 1.0 L of the same solvent. The crude methanol extract concentrate was filtered on this bed of charcoal and then washed with 1.5 L of dichloromethane:methanol (9:1). The collected mixture was evaporated under vacuum using a rotovap and the residue was left under high vacuum for one hour using a vacuum pump to remove all traces of methanol.

Example 2B

Liquid-Liquid Extraction

The crude methanolic extract concentrate was partitioned with a mixture containing methanol (400 ml), water (800 ml) and hexane (1100 ml) in a 5L separatory funnel. After allowing for the solvents to partition, the top layer with dark green color was tested and discarded, the lower aqueous phase was extracted with methylene chloride two times. The methylene chloride extracts from two partitions were combined and then concentrated to generate 270 ml of DCM extract concentrate containing the plurality of taxanes.

Example 3

Silica Gel Column Chromatography 318 g of silica gel (40-63 µm) was used to pack a lab 2-feet long column and 70 ml of the DCM extract concentrate (~21 g solid) was loaded onto the column followed by DCM/EtOAc elution: 7L of DCM/EtOAc 7:3 and 3L of DCM/EtOAc 1:1. 100 fractions were collected, each having a 100 ml volume. According to HPLC and TLC analyses, fractions were combined into five groups: paclitaxel containing fractions, cephalomannine and paclitaxel containing fractions, 9-DHB containing fractions, baccatin III containing fractions and 10-DAB containing fractions. The last four fractions (i.e., the waste stream fractions) can be combined into a pooled waste stream solution containing a plurality of taxanes, or can be used individually in further synthetic conversions. In the present case, after the paclitaxel containing fractions were eluted from the column, the remaining fractions were collected and pooled to form a waste taxane solution, which was further utilized in the following steps.

Example 4

Synthesis and Isolation of 10-Deacetylbaccatin III from a Waste Taxane Solution

Cleavage of C-10 and C-13 Ester Linkages

As noted above, any ester linkages at C-10 and C-13 positions of the taxanes in the waste taxane solution obtained from the above process can be cleaved by using reagents such as K-t-OBu, Li-t-OBu, LiHMDS, n-BuLi, LiOH and CH$_3$Li, or NaBH$_4$ and NaH in the presence of a Lewis acid, such as ZnCl$_2$. For example, the waste taxane solution was dissolved in THF and cooled to −40° C. under argon atmosphere. To the stirred solution at this temperature was added any one of the above reagents, such as, for example, K-t-OBu and the reaction was monitored by TLC. The reaction was further stirred at this temperature for a period between 30 minutes to 6 hrs until complete consumption of the starting material as evidenced by TLC. Additional amounts of the base (e.g., K-t-OBu) were added at this temperature, and the reaction was stirred for an additional hour, as necessary for complete consumption of the starting material. The reaction mixture was then worked up as usual. Evaporation of the solvent afforded a crude first intermediate mixture of C-10 and C-13 deprotected taxanes that could be used directly in the next step of the synthesis or could be further purified by column chromatography using mixtures of DCM/ethyl acetate and/or crystallized from a suitable solvent.

Protection of C-7 and C-10 Hydroxy Groups

The first intermediate mixture of C-10 and C-13 deprotected taxanes was dissolved in THF and stirred at −40° C. under argon atmosphere. To this stirred solution at −40° C. was added a base (such as DMAP, pyridine, TEA or any other base, such as LiOH, Li-t-OBu, n-BuLi, K-t-OBu, or a mixture of n-BuLi/K-t-OBu) followed by addition of a hydroxy-protecting group agent (such as triethyl silyl chloride or any other alkylating agent, or acetic anhydride, acetyl chloride, di-tert-butyl dicarbonate or any other acylating agent). The reaction was stirred at this temperature for a period between 30 minutes to 6 hrs until complete consumption of the initial starting material as evidenced by TLC and HPLC analysis. Additional amounts of the base and alkylating or acylating agent were added at this temperature, as necessary for complete consumption of the starting materials. The reaction mixture was then worked up as usual and the solvent removed to give a second intermediate mixture of C-7 and C-10 protected taxanes that could be used directly in the next step of the synthesis or purified by either column chromatography using mixtures of DCM/EtOAc or crystallized from a suitable solvent.

Chromatographic Separation 318 g of silica gel (40-63 μm) was used to pack a lab 2-feet long column and the second intermediate mixture was loaded onto the column followed by DCM/EtOAc elution: 7L of DCM/EtOAc 7:3 and 3L of DCM/EtOAc 1:1. 100 fractions were collected, each having a 100 ml volume. According to HPLC and TLC analyses, fractions were combined into two groups: fractions containing taxanes having a keto substituent at the C-9 position (i.e., protected 10-DAB derivatives) and taxanes having a hydroxy group at the C-9 position. The fractions containing taxanes having a hydroxy group at the C-9 position were pooled to yield a third intermediate mixture of C-9 hydroxy taxanes, which was further utilized in the following synthetic steps.

Oxidation of C-9 Hydroxy Groups

The third intermediate mixture of C-9 hydroxy taxanes was oxidized using an oxidizing agent to obtain a ketone at the C-9 position. This oxidation can be achieved using a variety of oxidants under mild conditions, including 4-(dimethylamino) pyridinium chlorochromate, pyridinium chlorochromate, chromium (IV) oxide-silica gel, chromium (IV) oxide-acetic acid (Fieser reagent) or acidic media, bromine, dimethyl sulfoxide-dicyclohexylcarbodiimide, and manganese dioxide with dichloro(p-cymene)-ruthenium (II).

The third intermediate mixture of C-9 hydroxy taxanes was dissolved in an organic solvent (such as acetone) and cooled to near 0° C. with continuous stirring. The oxidant was added to this solution at low temperature and the reaction was stirred for a period between 30 minutes to 6 hrs until complete consumption of the starting materials as evidenced by TLC. After completion of the reaction, the reaction was worked up as usual to afford a crude fourth intermediate mixture of C-9 oxidized taxanes that could be further purified (using silica gel column chromatography with mixtures of DCM/EtOAc for elution or crystallization from a suitable solvent) or used directly for the next step of the synthesis.

Deprotection of C-7 and C-10 Hydroxy Groups

As noted above, deprotection of the C-7 and C-10 hydroxy groups in the fourth intermediate mixture of C-9 oxidized taxanes can be accomplished by using reagents such as LiOH, n-BuLi, Li-t-OBu, CH$_3$Li, K-t-OBu, and LiHMDS for the deprotection of the C-10 hydroxy groups, and HF, HCl, TFA and acetic acid for the deprotection of the C-7 hydroxy groups.

The fourth intermediate mixture of C-9 oxidized taxanes was dissolved in THF and cooled to −40° C. under argon atmosphere. To the stirred solution at this temperature was added any one of the above bases, such as, for example, K-t-OBu and the reaction was monitored by TLC. The reaction was further stirred at this temperature for a period between 30 minutes to 6 hrs until complete consumption of the starting material as evidenced by TLC. The reaction mixture was then worked up as usual. Evaporation of the solvent afforded a crude mixture of C-10 deprotected taxanes that could be further deprotected at the C-7 position as described below, or could be further purified by column chromatography using mixtures of DCM/ethyl acetate and/or crystallized from a suitable solvent prior to deprotection at the C-7 position.

The crude mixture of C-10 deprotected taxanes was dissolved in pyridine, DCM or an organic solvent at room temperature. To this solution was added HF or TFA. After complete consumption of the starting material as evidenced by TLC, the reaction was worked up and purified by flash chromatography using mixtures of DCM/EtOAc to afford 10-deacetylbaccatin III, which could further be crystallized from a suitable solvent to give a product of >99% purity.

Example 5

Synthesis of Paclitaxel and Docetaxel from 10-Deacetylbaccatin III

The 10-deacetylbaccatin III obtained from the prior steps is then converted to paclitaxel and/or docetaxel according to, for example, the process set forth in U.S. Pat. No. 5,466,834, which application is incorporated herein by reference in its entirety.

Example 6

Synthesis of 10-Deacetylbaccatin III and Baccatin III from Waste Taxane Solution Protection of C-7 Hydroxy Groups and Cleavage of C-13 Ester Linkages The waste taxane solution obtained from the above process was dissolved in THF and stirred at −40° C. under argon atmosphere. To this stirred solution at −40° C. was added a base (such as DMAP, pyridine, TEA or any other lithium or potassium base, such as LiOH, Li-t-OBu, n-BuLi, K-t-OBu or a mixture of n-BuLi/K-t-OBu) followed by addition of a hydroxy-protecting group agent (such as triethylsilyl chloride or any other alkylating agent, or acetic anhydride, acetyl chloride, di-tert-butyl dicarbonate or any other acylating agent). The reaction was stirred at this temperature for a period between 30 minutes to 6 hrs until complete consumption of the initial starting material as evidenced by TLC and HPLC analysis. Additional amounts of the base and alkylating or acylating agent were added at this temperature, as necessary for complete consumption of the starting materials and to ensure cleavage of the C-13 ester linkages. Further amounts of the base may be added to ensure cleavage of the C-10 ester linkages. The reaction mixture was then worked up as usual and the solvent removed to give a crude first intermediate mixture of C-7 protected taxanes that could be used directly in the next step of the synthesis or purified by either column chromatography using mixtures of DCM/EtOAc or crystallized from a suitable solvent.

Oxidation of C-9 Hydroxy Groups

The first intermediate mixture of C-7 protected taxanes was oxidized using an oxidizing agent to obtain a ketone at the C-9 position. This oxidation for the first intermediate mixture of C-7 protected taxanes can be achieved using a variety of oxidants under mild conditions, including 4-(dimethylamino)pyridinium chlorochromate, pyridinium chlorochromate, chromium (IV) oxide-silica gel, chromium (IV) oxide-acetic acid (Fieser reagent) or acidic media, bromine, dimethyl sulfoxide-dicyclohexylcarbodiimide, and manganese dioxide with dichloro(p-cymene)-ruthenium (II).

The first intermediate mixture of C-7 protected taxanes was dissolved in an organic solvent (such as acetone) and cooled to near 0° C. with continuous stirring. The oxidant was added to this solution at low temperature and the reaction was stirred for a period between 30 minutes to 6 hrs until complete consumption of the starting materials as evidenced by TLC. After completion of the reaction, the reaction was worked up as usual to afford a crude second intermediate mixture of C-7 protected taxanes that could be further purified (using silica gel column chromatography with mixtures of DCM/EtOAc for elution or crystallization from a suitable solvent) or used directly for the next step of the synthesis.

Deprotection of C-7 Hydroxy Groups

As noted above, deprotection of the C-7 hydroxy groups in the second intermediate mixture of C-7 protected taxanes can be accomplished by using an acid, such as, HF, HCl, TFA or acetic acid.

The second intermediate mixture of C-7 protected taxanes was dissolved in pyridine or an organic solvent at room temperature. To this solution was added HF, or any other acid such as HCl, TFA or acetic acid. After complete consumption of the starting material, as evidenced by TLC, the reaction was worked up as usual and purified by flash chromatography using mixtures of DCM/EtOAc to afford a mixture of 10-deacetylbaccatin III and baccatin III, that could further be crystallized from a suitable solvent to give a product of >99% purity.

Example 7

Synthesis of Paclitaxel and Docetaxel from 10-Deacetylbaccatin III and Baccatin III The mixture of 10-deacetylbaccatin III and baccatin III is then converted to paclitaxel and/or docetaxel according to, for example, the process set forth in U.S. Pat. No. 5,466,834, which application is incorporated herein by reference in its entirety.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The invention claimed is:

1. A process comprising:
   preparing 10-deacetylbaccatin III by
   (1) providing an initial mixture comprising 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol;
   (2) prior to steps 3, 4 and 5, cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;
   (3) separating the taxanes in the first intermediate mixture having a keto substituent at the C-9 position from the taxanes in the first intermediate mixture having a hydroxy group at the C-9 position to yield 10-deacetylbaccatin III and a second intermediate mixture of C-9 hydroxy taxanes;
   (4) protecting the hydroxy groups at the C-7 and C-10 positions of each taxane in the second intermediate mixture to yield a third intermediate mixture of C-7 and C-10 protected taxanes;
   (5) oxidizing the hydroxy group at the C-9 position of each taxane in the third intermediate mixture to yield a fourth intermediate mixture of C-9 oxidized taxanes; and
   (6) deprotecting the hydroxy groups at the C-7 and C-10 positions of each taxane in the fourth intermediate mixture to yield 10-deacetylbaccatin III.

2. The process of claim 1 wherein the step of cleaving the ester linkages at the C-10 and C-13 positions of each taxane in the initial mixture comprises contacting the initial mixture with:
   a base selected from the group consisting of K-t-OBu, Li-t-OBu, LiHMDS, n-BuLi, LiOH and $CH_3Li$; or
   a reducing salt comprising a reducing agent selected from $NaBH_4$ and NaH and a Lewis acid.

3. The process of claim 2 wherein the step of cleaving the ester linkages at the C-10 and C-13 positions of each taxane in the initial mixture comprises contacting the initial mixture with K-t-OBu.

4. The process of claim 1 wherein the step of protecting the hydroxy groups at the C-7 and C-10 positions of each taxane in the second intermediate mixture comprises contacting the second intermediate mixture with a base and a hydroxy-protecting group in an organic solvent, and wherein:
   the base is selected from the group consisting of DMAP, pyridine, TEA, LiOH, Li-t-OBu, n-BuLi, K-t-OBu and a mixture of n-BuLi/K-t-OBu; and
   the hydroxy-protecting group is selected from the group consisting of alkylating agents and acylating agents.

5. The process of claim 4 wherein the hydroxy-protecting group is selected from the group consisting of tert-butoxycarbonyl, benzyloxycarbonyl, 2,2,2-trichloroethoxycarbonyl, dichloroacetyl and acetyl.

6. The process of claim 5 wherein the base of DMAP and the hydroxy-protecting group is tert-butoxycarbonyl.

7. The process of claim 1 wherein the step of oxidizing the hydroxy group at the C-9 position of each taxane in the third intermediate mixture comprises contacting the third intermediate mixture with an oxidizing agent selected from the group consisting of 4-(dimethylamino)pyridinium chlorochromate, pyridinium chlorochromate, chromium (IV) oxide-silica gel, chromium (IV) oxide-acetic acid, bromine, dimethyl sulfoxide-dicyclohexylcarbodiimide, and manganese dioxide with dichloro(p-cymene)-ruthenium (II).

8. The process of claim 7 wherein the oxidizing agent is chromium (IV) oxide-silica gel.

9. The process of claim 1 wherein the step of deprotecting the hydroxy groups at the C-7 and C-10 positions of each taxane in the fourth intermediate mixture comprises the steps of:
  deprotecting the hydroxy groups at the C-10 positions of each taxane in the fourth intermediate mixture; and
  deprotecting the hydroxy groups at the C-7 positions of each taxane in the fourth intermediate mixture.

10. The process of claim 9 wherein the step of deprotecting the hydroxy groups at the C-10 positions of each taxane in the fourth intermediate mixture comprises contacting the fourth intermediate mixture with a base selected from the group consisting of LiOH, n-BuLi, Li-t-OBu, $CH_3Li$, K-t-OBu and LiHMDS.

11. The process of claim 9 wherein the step of deprotecting the hydroxy groups at the C-7 position of each taxane in the fourth intermediate mixture comprises contacting the fourth intermediate mixture with an acid selected from the group consisting of HF, TFA, HCI and acetic acid.

12. The process of claim 1 further comprising converting the 10-deacetylbaccatin III obtained from steps (2) and (5) to paclitaxel and docetaxel.

13. A process comprising:
  preparing 10-deacetylbaccatin III from an initial mixture comprising 9-dihydro-13-acetylbaccatin III, and at least one additional taxane selected from paclitaxel, 10-deacetylbaccatin III, baccatin III, cephalomannine, 10-deacetyl taxol, 7-xylosyl taxol and 10-deacetyl-7-xylosyl taxol, the process including
  (1) prior to steps 3, 4 and 5, cleaving the ester linkages at the C-10 and C-13 positions of each taxane in the initial mixture having an ester linkage at one or both of the C-10 and C-13 positions to yield a first intermediate mixture of C-10 and C-13 deprotected taxanes;
  (2) protecting the hydroxy groups at the C-7 and C-10 positions of each taxane in the first intermediate mixture having a hydroxy group at one or both of the C-7 and C-10 positions to yield a second intermediate mixture of C-7 and C-10 protected taxanes;
  (3) separating the taxanes in the second intermediate mixture having a keto substituent at the C-9 position from the taxanes in the second intermediate mixture having a hydroxy group at the C-9 position to yield C-7 and C-10 protected 10-deacetylbaccatin III and a third intermediate mixture of C-9 hydroxy taxanes;
  (4) oxidizing the hydroxy group at the C-9 position of each taxane in the third intermediate mixture to yield a fourth intermediate mixture of C-9 oxidized taxanes; and
  (5) deprotecting the hydroxy groups at the C-7 and C-10 positions of each taxane in the fourth intermediate mixture to yield 10-deacetylbaccatin III.

14. The process of claim 13 wherein the step of cleaving the ester linkages at the C-10 and C-13 positions of each taxane in the initial mixture comprises contacting the initial mixture with:
  a base selected from the group consisting of K-t-OBu, Li-t-OBu, LiHMDS, n-BuLi, LiOH and $CH_3Li$; or
  a reducing salt comprising a reducing agent selected from $NaBH_4$ and NaH and a Lewis acid.

15. The process of claim 14 wherein the step of cleaving the ester linkages at the C-10 and C-13 positions of each taxane in the initial mixture comprises contacting the initial mixture with K-t-OBu.

16. The process of claim 13 wherein the step of protecting the hydroxy groups at the C-7 and C-10 positions of each taxane in the first intermediate mixture comprises contacting the first intermediate mixture with a base and a hydroxy-protecting group in an organic solvent, and wherein:
  the base is selected from the group consisting of DMAP, pyridine, TEA, LiOH, Li-t-OBu, n-BuLi, K-t-OBu and a mixture of n-BuLi/K-t-OBu; and
  the hydroxy-protecting group is selected from the group consisting of alkylating agents and acylating agents.

17. The process of claim 16 wherein the hydroxy-protecting group is selected from the group consisting of tert-butoxycarbonyl, benzyloxycarbonyl, 2,2,2-trichloroethoxycarbonyl, dichloroacetyl and acetyl.

18. The process of claim 17 wherein the base is DMAP and the hydroxy-protecting group is tert-butoxycarbonyl.

19. The process of claim 13 wherein the step of oxidizing the hydroxy group at the C-9 position of each taxane in the third intermediate mixture comprises contacting the third intermediate mixture with an oxidizing agent selected from the group consisting of 4-(dimethylamino)pyridinium chlorochromate, pyridinium chlorochromate, chromium (IV) oxide silica gel, chromium (IV) oxide acetic acid, bromine, dimethyl sulfoxide-dicyclohexylcarbodiimide, and manganese dioxide with dichloro(p-cymene)-ruthenium (II).

20. The process of claim 19 wherein the oxidizing agent is chromium (IV) oxide-silica gel.

21. The process of claim 13 wherein the step of deprotecting the hydroxy groups at the C-7 and C-10 positions of each taxane in the fourth intermediate mixture comprises the steps of:
  deprotecting the hydroxy groups at the C-10 positions of each taxane in the fourth intermediate mixture; and
  deprotecting the hydroxy groups at the C-7 position of each taxane in the fourth intermediate mixture.

22. The process of claim 21 wherein the step of deprotecting the hydroxy groups at the C-10 positions of each taxane in the fourth intermediate mixture comprises contacting the fourth intermediate mixture with a base selected from the group consisting of LiOH, n-BuLi, Li-t-OBu, $CH_3Li$, K-t-OBu and LiHMDS.

23. The process of claim 21 wherein the step of deprotecting the hydroxy groups at the C-7 position of each taxane in the fourth intermediate mixture comprises contacting the fourth intermediate mixture with an acid selected from the group consisting of HF, TFA, HCI and acetic acid.

24. The process of claim 13 further comprising converting the 10-deacetylbaccatin III obtained from steps (2) and (5) to paclitaxel or docetaxel.

25. The process of claim 1 wherein the initial mixture comprises 9-dihydro-13-acetylbaccatin III, and at least two additional taxanes selected from paclitaxel, 10-deacetylbaccatin III, baccatin III, cephalomannine, 10-deacetyl taxol, 7-xylosyl taxol and 10-deacetyl-7-xylosyl taxol.

26. The process of claim 1 wherein the initial mixture comprises 9-dihydro-13-acetylbaccatin III, and at least three additional taxanes selected from paclitaxel, 10-deacetylbaccatin III, baccatin III, cephalomannine, 10-deacetyl taxol, 7-xylosyl taxol and 10-deacetyl-7-xylosyl taxol.

27. The process of claim 1 wherein the initial mixture comprises 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol.

28. The process of claim 1 wherein the initial mixture of taxanes is a waste taxane solution comprising one or more of the following:
pooled waste stream fractions collected during a chromatographic separation of a crude or partially purified taxane extract; and
pooled waste mother liquors collected during a recrystallization of a crude or partially purified taxane extract.

29. The process of claim 28 wherein the waste taxane solution comprises pooled waste stream fractions collected during a chromatographic separation of a crude taxane extract.

30. The process of claim 28 wherein the waste taxane solution comprises pooled waste stream fractions collected during chromatographic separations of both crude and partially purified taxane extracts and pooled waste mother liquors collected during recrystallizations of both crude and partially purified taxane extracts.

31. The process of claim 28 wherein the crude or partially purified taxane extracts are obtained from taxane-containing materials from the genus *Taxus*.

32. A process comprising:
preparing 10-deacetylbaccatin III and baccatin III from an initial mixture comprising 9-dihydro-13-acetylbaccatin III or cephalomannine, and at least one additional taxane selected from paclitaxel, 10-deacetylbaccatin III, baccatin III, 9-dihydro-13-acetylbaccatin III, cephalomannine, 10-deacetyl taxol, 7-xylosyl taxol and 10-deacetyl-7-xylosyl taxol, including the steps of:
protecting the hydroxy group at the C-7 position of each taxane in the initial mixture having a hydroxy group at the C-7 position and cleaving the ester linkage at the C-13 position of each taxane in the initial mixture having an ester linkage at the C-13 position to yield a first intermediate mixture of C-7 protected taxanes;
oxidizing the hydroxy group at the C-9 position of each taxane in the first intermediate mixture having a hydroxy group at the C-9 position to yield a second intermediate mixture of C-7 protected taxanes; and
deprotecting the hydroxy group at the C-7 position of each taxane in the second intermediate mixture to yield 10-deacetylbaccatin III and baccatin III.

33. The process of claim 32 wherein the step of protecting the hydroxy group at the C-7 position of each taxane in the initial mixture and cleaving the ester linkage at the C-13 position of each taxane in the initial mixture further comprises cleaving the ester linkage at the C-10 position of at least one taxane in the initial mixture having an ester linkage at the C-10 position.

34. The process of claim 32 wherein:
the step of protecting the hydroxy group at the C-7 position of each taxane in the initial mixture and cleaving the ester linkage at the C-13 position of each taxane in the initial mixture comprising contacting the initial mixture with a base and a hydroxy-protecting group in an organic solvent;
the base is selected from the group consisting of DMAP, pyridine, TEA, LiOH, Li-t-OBu n-BuLi, K-t-OBu and a mixture of n-BuLi/K-t-OBu; and
the hydroxy-protecting group is selected from the group consisting of alkylating agents and acylating agents.

35. The process of claim 34 wherein the hydroxy-protecting group is selected from the group consisting of tert-butoxycarbonyl, benzyloxycarbonyl, 2,2,2-trichloroethoxycarbonyl, dichloroacetyl and acetyl.

36. The process of claim 35 wherein the base is DMAP and the hydroxy-protecting group is tert-butoxycarbonyl.

37. The process of claim 32 wherein cleaving the ester linkage at the C-13 position of each taxane in the initial mixture comprises contacting the initial mixture with a base.

38. The process of claim 32 wherein the step of oxidizing the hydroxy group at the C-9 position of each taxane in the first intermediate mixture comprises contacting the first intermediate mixture with an oxidizing agent selected from the group consisting of 4-(dimethylamino)pyridinium chlorochromate, pyridinium chlorochromate, chromium (IV) oxide-silica gel, chromium (IV) oxide-acetic acid, bromine, dimethyl sulfoxide-dicyclohexylcarbodiimide, and manganese dioxide with dichloro(p-cymene)-ruthenium (II).

39. The process of claim 38 wherein the oxidizing agent is chromium (IV) oxide-silica gel.

40. The process of claim 32 wherein the step of deprotecting the hydroxy group at the C-7 position of each taxane in the second intermediate mixture comprises contacting the second intermediate mixture with an acid.

41. The process of claim 40 wherein the acid is selected from the group consisting of HF, TFA, HCl and acetic acid.

42. The process of claim 32 wherein the initial mixture comprises 9-dihydro-13-acetylbaccatin III or cephalomannine, and at least two additional taxanes selected from paclitaxel, 10-deacetylbaccatin III, baccatin III, 9-dihydro-13-acetylbaccatin III, cephalomannine, 10-deacetyl taxol, 7-xyloxyl taxol and 10-deacetyl-7-xyloxyl taxol.

43. The process of claim 32 wherein the initial mixture comprises 9-dihydro-13-acetylbaccatin III or cephalomannine and at least three additional taxanes selected from paclitaxel, 10-deacetylbaccatin III, baccatin III, 9-dihydro-13-acetylbaccatin III, cephalomannine, 10-deacetyl taxol, 7-xylosyl taxol and 10-deacetyl-7-xylosyl taxol.

44. The process of claim 32 wherein the initial mixture comprises 9-dihydro-13-acetylbaccatin III, paclitaxel, 10-deacetylbaccatin III, baccatin III, cephalomannine, 10-deacetyl taxol, 7-xylosyl taxol and 10-deacetyl-7-xylosyl taxol.

45. The process of claim 32 wherein the initial mixture of taxanes is a waste taxane solution comprising one or more of the following:
pooled waste stream fractions collected during a chromatographic separation of a crude or partially purified taxane extract; and
pooled waste mother liquors collected during a recrystallization of a crude or partially purified taxane extract.

46. The process of claim 45 wherein the waste taxane solution comprises pooled waste stream fractions collected during a chromatographic separation of a crude taxane extract.

47. The process of claim 45 wherein the waste taxane solution comprises pooled waste stream fractions collected during chromatographic separations of both crude and partially purified taxane extracts and pooled waste mother liquors collected during recrystallizations of both crude and partially purified taxane extracts.

48. The process of claim 45 wherein the crude and partially purified taxane extracts are obtained from taxane-containing materials from the genus *Taxus*.

49. The process of claim 32 further comprising protecting the hydroxy group at the C-7 position of each of the 10-deacetylbaccatin III and baccatin III and converting the protected 10-deacetylbaccatin III and baccatin III to paclitaxel or docetaxel.

* * * * *

UNITED STATES PATENT AND TRADEMARK OFFICE
CERTIFICATE OF CORRECTION

PATENT NO. : 7,838,694 B2  
APPLICATION NO. : 11/587407  
DATED : November 23, 2010  
INVENTOR(S) : Ragina Naidu et al.

Page 1 of 1

It is certified that error appears in the above-identified patent and that said Letters Patent is hereby corrected as shown below:

In the Specification:

In column 4, lines 23-24, the words "each processes according to this aspect of the present invention comprise" should be --each of the processes according to this aspect of the present invention comprises--.

In column 6, line 63, the word "six" should be --sixth--.

In column 10, line 52, the numbers and words "6 to 20 carbon" should be --6 to 20 carbons--.

In column 16, line 22, the word "baccatin" should be --baccatin.--.

In column 17, line 64, the referenced patent number "6,139,989" should be --6,136,989--.

In column 19, line 52, the referenced patent number "6,139,989" should be --6,136,989--.

In column 22, line 38, the word "Chromatographv" should be --Chromatography--.

In the Claims:

In column 26, line 60, the word "dichioroacetyl" should be --dichloroacetyl--.

In column 27, line 26, the word "HCI" should be --HC1--.

In column 28, line 51, the word "HCI" should be --HC1--.

In column 29, line 58, the words "Li-t-OBu n-BuLi," should be --Li-t-OBu, n-BuLi--.

In column 30, line 21, the word "HCI" should be --HC1--.

In column 30, line 27, the compound word "7-xyloxyl" should be --7-xylosyl--.

Signed and Sealed this  
Thirteenth Day of November, 2012

David J. Kappos  
*Director of the United States Patent and Trademark Office*